United States Patent
Su et al.

(10) Patent No.: US 6,841,375 B2
(45) Date of Patent: Jan. 11, 2005

(54) FLAVOBACTERIUM HEPARINUM EXPRESSION SYSTEM

(75) Inventors: Hongsheng Su, Kirkland (CA); Zhongqi Shao, Dollard-des-Ormeaux (CA); Ana Lydia Tkalec, St. Leonard (CA); Francoise Blain, LaSalle (CA); Joseph Zimmerman, Elm Grove, WI (US)

(73) Assignee: BioMarin Pharmaceuticals Inc., Novato, CA (US)

( * ) Notice: Subject to any disclaimer, the term of this patent is extended or adjusted under 35 U.S.C. 154(b) by 24 days.

(21) Appl. No.: 09/766,873

(22) Filed: Jan. 19, 2001

(65) Prior Publication Data

US 2001/0034043 A1 Oct. 25, 2001

Related U.S. Application Data

(60) Provisional application No. 60/177,568, filed on Jan. 21, 2000.

(51) Int. Cl.[7] .............................. C12N 1/20; C07H 21/04
(52) U.S. Cl. .................................. 435/252.3; 435/320.1; 435/69.1; 435/243; 435/471; 435/473; 435/476; 435/91.1; 536/23.1; 536/23.2; 536/23.7
(58) Field of Search ............................... 536/23.1, 23.2, 536/23.7; 435/252.3, 69.1, 320.1, 243, 471, 473, 476, 91.1

(56) References Cited

U.S. PATENT DOCUMENTS 5,695,968 A    12/1997 Nanba et al. ............... 435/106

FOREIGN PATENT DOCUMENTS

WO        WO 96/01894    *  1/1996

OTHER PUBLICATIONS

McBride et al., Development of Techniques to Genetically Manipulate Members of the Genera Cytophaga, Flavobacterium, Flexibacter, and Sporocytophaga, Applied and Environmental Microbiology, vol. 62, No. 8, pp. 3017–3022, Aug. 1996.*

Christensen, "Description and Taxonomic Status of Cytophaga heparina (Payza and Korn) comb. nov. (Basionym: Flavobacterium heparinum Payza and Korn 1956)" Int. J. Syst. Bacteriol. 1980 30:473–475.

Takeuchi and Yokota, "Proposals of Sphingobacterium faecium Sp. Nov., Sphingobacterium piscium Sp. Nov., Sphingobacterium heparinum Comb. Nov., Sphingobacterium thalpophilum Comb. Nov. and Two Genospecies of the Genus Sphingobacterium, and Synonymy of Flavobacterium yabuuchiae and Sphingobacterium spiritvorum" J. Gen. Appl. Microbiol. 1992 38:465–482.

Steyn, P. L. et al., "Classification of Heparinolytic Bacteria Into A New Genus, Pedobacter, Comprising Four Species: Pedobacter heparinus Comb. Nov., Pedobacter piscium Comb. Nov., Pedobacter africanus Sp. Nov. and Pedobacter saltans sp. nov. Proposal of the family Sphingobacteriaceae Fam. Nov." Int. J. Syst. Bacteriol. 1998 48:165–177.

Antoine, et al., "Isolation and Molecular Characterization of a Novel Broad–Host–Range Plasmid From Bordetella bronchiseptica With Sequence Similarities To Plasmids From Gram–positive Organisms" Molecular Microbiology (1992) vol. 6, No. 13, pp. 1785–1799.

* cited by examiner

Primary Examiner—Richard Hutson
(74) Attorney, Agent, or Firm—Wilmer Cutler Pickering Hale and Dorr LLP

(57) ABSTRACT

This invention is directed to Flavobacterium heparinum for use as a host cell organism for the expression of homologous and heterologous genes.

9 Claims, 1 Drawing Sheet

EXPRESSION VECTOR, pIBXF2

EXPRESSION VECTOR, pIBXF2

INTEGRATION VECTOR, pIBXF1

FLAVOBACTERIUM HEPARINUM EXPRESSION SYSTEM

FIELD OF THE INVENTION

The present invention is in the area of a novel procaryotic expression system and, in particular, a *Flavobacterium heparinum* host system for the expression of gene products.

BACKGROUND OF THE INVENTION

Genetic engineering has made it possible to produce large amounts of heterologous proteins or polypeptides in bacterial cells by means of recombinant expression systems. The expressed heterologous proteins may be mammalian, other eukaryo tic, viral, bacterial, cyanobacterial, archeabacterial or of synthetic origin.

The bacterial host cell of choice for expression of recombinant DNA has long been *Escherichia coli*. However, this microorganism has many disadvantages as a host cell including the inability to secrete recombinantly produced proteins, the precipitation of highly expressed recombinantly produced proteins into inclusion bodies within the cell, the inability to glycosylate recombinantly produced proteins and the difficulties faced when purifying a recombinantly produced protein from *E. coli*.

The DNA sequences and methods for the expression of homologous and heterologous proteins in *Flavobacterium heparinum*, a Gram negative, non-pathogenic soil bacterium, have not been investigated. The ability to express heterologous and homologous polypeptides and proteins in *F. heparinum* would be desirable as the microorganism naturally produces glycosylated proteins. Thus, *F. heparinum* would be useful as a host cell for expression of recombinant DNA encoding mammalian proteins since they are often glycosylated. In addition, *F. heparinum* naturally produces low levels of the glycosaminoglycan degrading enzymes that act upon heparin and other glycosaminoglycans. The heparinase enzymes have significant medical utility and the production of these enzymes from their natural source would be desirable.

It is an object of the invention to provide nucleic acids and expression systems for the expression of recombinant DNA molecules in *F. heparinum*. Another object of the invention is to provide methods for use of *F. heparinum* as a host cell for the expression of recombinant DNA molecules.

SUMMARY OF THE INVENTION

It has been discovered that *F. heparinum* is useful as a host cell for the expression of recombinant DNA sequences. One aspect of the present invention provides a method which achieves expression of homologous and heterologous genes in *F. heparinum* and the coupling of expression to secretion to produce a biologically active polypeptide or protein. Further, an expression system for cloned gene sequences comprising the host, nucleotide sequences encoding a polypeptide or protein of interest, and a vector. In a preferred embodiment of the system, the vector for expression of homologous and heterologous sequences comprises a functional origin of replication (OriC) from *F. heparinum* or another functional origin of replication, replication (rep) genes which direct the replication of the vector, a promoter derived from a gene endogenous to the *F. heparinum* host. In another preferred embodiment, the vector for expression of homologous and heterologous sequences comprises a chromosomal integration sequence. In a further embodiment, the expression vector further comprises selective markers and/or a regulated promoter for the expression of desired gene sequences.

The overexpression of homologous and heterologous cloned genes in the *F. heparinum* host cell, and the suitability of *F. heparinum* for the expression of recombinant proteins is demonstrated by the expression of the enzymes, heparinase I, heparinase II, heparinase III, chondroitinase AC, and chondroitinase B from *F. heparinum*; dhfrII and β-galactosidase encoding genes from *E. coli*.

DETAILED DESCRIPTION OF THE INVENTION

Figure 1:
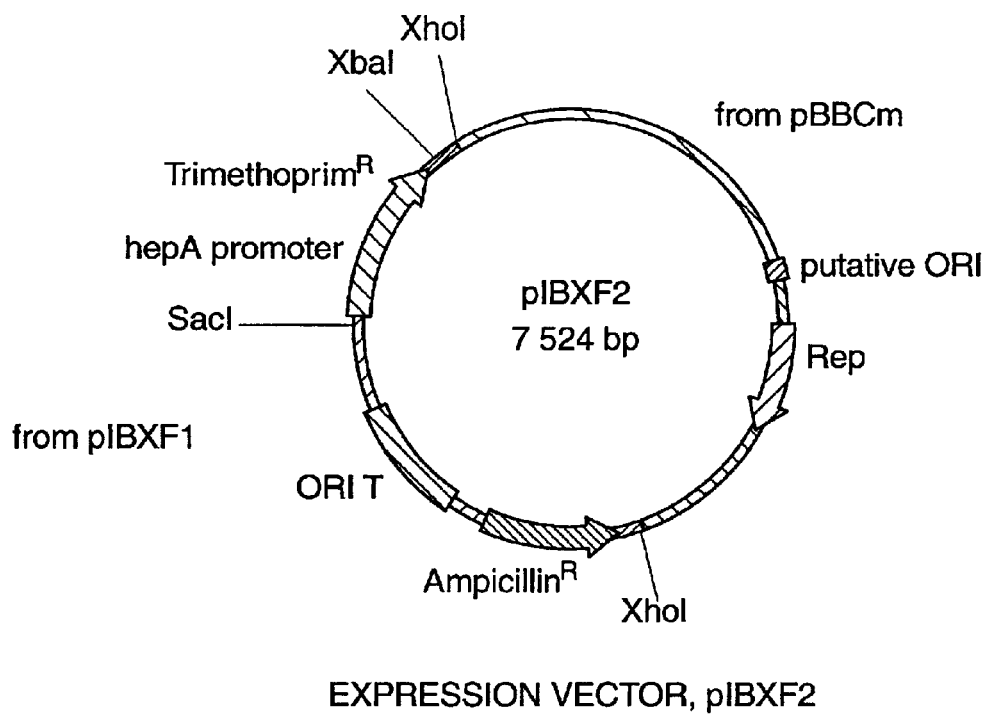
FIG. 1 is a schematic diagram of plasmid pIBXF2 which is derived from plasmid pBBCm.
Figure 2:
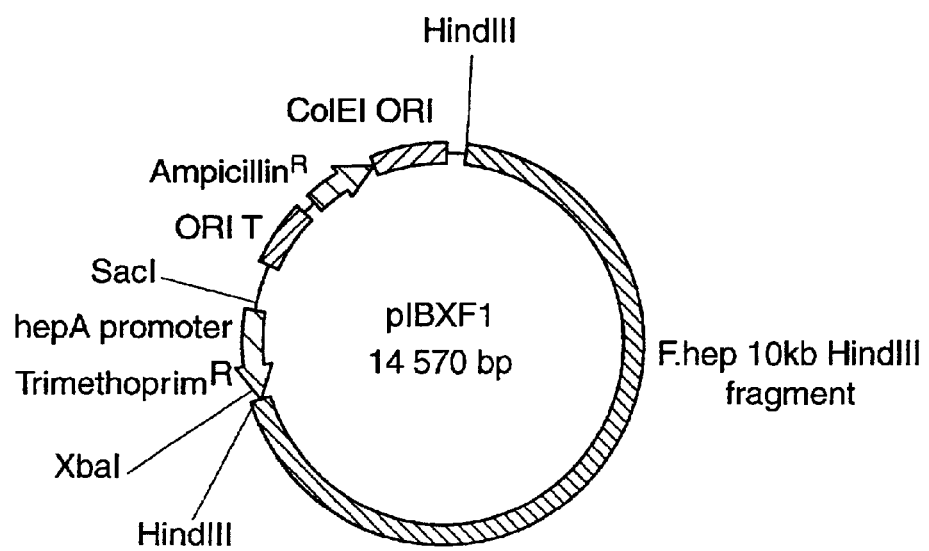
FIG. 2 is a schematic diagram of the integration vector pIBXF1.

The invention is the use of the bacterium *Flavobacterium heparinum* for the expression of homologous and heterologous genes. The invention provides nucleic acids and expression systems for the expression of recombinant DNA molecules in *F. heparinum*. The invention further provides methods for introducing vectors and other recombinant DNA into *F. heparinum*.

Definitions

"Biologically active." The term "biologically active" as used herein in relation to homologous or heterologous polypeptides or proteins expressed in the *F. heparinum* host cell denotes that the polypeptide or protein is produced in an appropriate conformation for obtaining biological activity, rather than a misfolded, aggregated and insoluble form which requires special denaturation and renaturation measures to achieve an appropriate conformation to any substantial extent. The term therefore includes polypeptide precursors of biologically active proteins, which are not themselves biologically active, but which can be readily converted into their biologically active forms.

"Foreign" or "heterologous" or "non-bacterial"; "native" or "homologous". A "foreign" or "heterologous" polypeptide is a peptide which is not normally found in a host cell of a particular species. The nucleic acid encoding such a polypeptide is also referred to as "foreign" or "heterologous." For example, insulin-like growth factor (IGF), insulin-like growth factor binding protein (IGFBP), and transforming growth factor-Beta (TGF-β) are native to mammalian cells and human rhinovirus 3C protease is native to viruses and virally-infected mammalian cells, but these proteins are foreign or heterologous to *F. heparinum*. A "non-bacterial protein" is a protein or polypeptide which is not naturally found in a bacterial cell. Non-bacterial proteins include viral and eukaryotic proteins. Non-bacterial, foreign, or heterologous proteins may also be fusions between non-bacterial, foreign, or heterologous proteins and other proteins or polypeptides. For the embodiments encompassed by this invention, both "heterologous protein" and "non-bacterial protein" may be expressed. As disclosed herein, genes encoding heterologous or non-bacterial proteins of interest do not contain promoters functional in the host cell. The genes must be linked to a separate promoter that is functional in the host cell in order to be expressed. A "native" or "homologous" polypeptide or DNA sequence, by contrast, is commonly found in the host cell. A promoter or other sequence effecting, for example, the transcription or translation of a gene is also considered "homologous" if it is functional in the host cell. For example, a hepA gene (coding for heparinase I) is considered "homologous" to a *F. heparinum* host cell, since, the encoded protein, heparinase I, is naturally produced by the cell.

"Genes encoding heterologous, foreign or non-bacterial proteins". "Genes encoding heterologous, foreign or non-bacterial proteins" contain all of the genetic elements necessary for the expression of the heterologous, foreign or non-bacterial protein with the exception of a promoter functional in the host cell. These genes encompass recombinant genes which may include genetic elements native to the host cell. Further, the coding regions of these genes may optionally be optimized for the codon usage of the host cell.

"Operably linked". A nucleic acid sequence is operably linked when it is placed into a functional relationship with another nucleic acid sequence. For example, a promoter is operably linked to a coding sequence if the promoter affects its transcription or expression. Generally, DNA sequences which are operably linked are contiguous and, where necessary, in reading frame.

"Recombinant". A "recombinant" nucleic acid is one which is made by the joining of two otherwise separated segments of nucleic acid sequence in vitro or by chemical synthesis.

"Vector". A "vector" is a carrier DNA molecule into which a nucleic acid sequence can be inserted for introduction into a host cell and the inserted nucleic acid sequences may be expressed. A vector may replicate autonomously in the host cell or be integrated into the host cell genome.

As detailed below, there are a number of methods and variables to consider in the construction of an expression system using *F. heparinum* as the host. Depending on the protein to be expressed and the degree of regulation and quality of expression desired, the system can consist of as little as the host and an expression vector containing transcription and translation signals and the gene to be expressed. To control the rate and extent of expression, the gene of interest may be placed under the control of an inducible promoter or a constitutively expressed promoter, or the promoter can be placed under the control of a repressor or stimulatory protein.

The first consideration is to determine the polypeptide or protein to be expressed, and to isolate a sequence encoding some or all of the protein. Methods for the isolation of protein-encoding sequences are well known to those of ordinary skill in the art of genetic engineering. Examples of the isolation and characterization of the exemplary proteins are provided below.

The second consideration is the selection and/or construction of a vector, such as a plasmid which provides for homologous recombination or other recombinant DNA having an origin of replication, and transposable elements, including bacteriophage systems, transposons and insertion sequences The plasmid system can be a broad-host or narrow-host plasmid. General techniques for nucleic acid manipulation useful for the practice of the claimed invention are described generally, for example, in Sambrook et al., "Molecular Cloning: A Laboratory Manual", Vols. 1–3 (Cold Spring Harbor Laboratory Press, 2 ed., 1989) or in Ausubel et al., Current Protocols in Molecular Biology (Green Publishing and Wiley-Interscience: New York, 1987).

Useful vectors will preferentially be a modified broad-host plasmid which can replicate in *F. heparinum*, or a vector containing a DNA fragment which can facilitate the homologous recombination. In addition, a vector will include restriction enzyme sites for insertion of foreign DNA and one or more selectable markers. Commonly used selectable markers are genes that confer resistance to antibiotics such as ampicillin, tetracycline, chloramphenicol, erythromycin, and trimethoprim. Additional selectable markers include genes which encode for heavy metal resistance, such as mercuric reductase, or a nutritional requirement factor, such as an amino acid requirement factor. A preferred selectable marker is the trimethoprim-resistance dihydrofolate reductase II gene. The selective marker preferably is regulated by a regulatory region from *F. heparinum*. Useful regulatory regions include the heparinase I gene regulatory region. Other useful plasmids, and the genetic engineering methods for inserting genes of interest into the plasmid will be apparent to those of ordinary skill in the art.

Optionally, the desired protein encoded by the recombinant DNA can be genetically engineered to be secreted by the addition of secretion signals and processing signals in operative association with the nucleic acid sequence encoding the desired protein. The molecular techniques to engineer a vector to include secretion and processing signals are well known to those of ordinary skill in the art.

Once the nucleotide sequence and the vector have been selected, sequences for the expression, regulation of expression, an post-translational characteristics of the expression protein can be isolated and inserted into the vector. A number of promoters are useful in the present invention, including the promoters for the homologous genes hepA and lysA and heterologous promoters.

A variety of methods for introducing nucleic acids into host cells are known in the art, including, but not limited to, electroporation; transfection employing calcium chloride, rubidium chloride calcium phosphate; DEAE-dextran, or other substances; microprojectile bombardment; lipofection; and infection (where the vector is an infectious agent, such as a retroviral genome). See generally, Sambrook et al., supra and Ausubel et al., supra. Methods for bacterial transformation by plasmid DNA have been developed to optimize the efficiency of DNA uptake. Generally, the bacterial cells are treated to render them competent to incorporate plasmid DNA, and then once inside, the selectable marker allows the transformed cells to survive in the presence of the selected medium.

Some plasmids can bring about their own transfer by the conjugation process, as is well understood in the art. Briefly, a cell extrudes a sex pilus, which is coded for by plasmid genes, which adheres to a neighboring cell, and the cells are then drawn into direct contact. The plasmid then undergoes transfer replication and one parental strand passes to the recipient cell and one strand remains in the donor cell. Complementary strands are synthesized both in the donor and recipient cells simultaneously with the transfer. The daughter molecules are circularized by ligase action immediately after the transfer replication is complete. The mating cells then break apart.

Other methods can achieve either or both of these results by transfer and integration of DNA into a suitable site on the chromosome. The transferred DNA comprises a DNA fragment encoding a selectable marker and a homologous DNA sequence from the host. Optionally, a transferred DNA may also comprise, in an operable linkage to the sequence encoding the homologous DNA, transcription and translation initiation regulatory sequences and expression control sequences, which may include a promoter, an enhancer and necessary processing information sites, such as ribosome-binding sites, and mRNA stabilizing sequences, as well as any necessary secretion signals, where appropriate, which allow the expressed polypeptide or protein to cross and/or lodge in cell membranes, and thus attain its functional topology, or be secreted from the cell. Alternatively, integration of a gene of interest near a promoter on the *F. heparinum* chromosome can be designed to result in a operable linkage (for example, by integrating a transferred DNA into an operon on the chromosome). The site of integration or sequences adjacent to the site of integration may facilitate amplification (e.g. where the site is located in a transposable element, by providing duplicate DNA sequences, or even by providing a region of DNA sequence homologous to a portion of the chromosomal transfer DNA, thus providing duplicate DNA sequences).

EXAMPLES

The following examples are provided to illustrate the invention, but are not intended to, and should not be construed to, in any way limit the scope of the invention as defined by the claims which follow.

The Examples do not include detailed descriptions for conventional methods employed in the construction of plasmids, the insertion of genes encoding polypeptides into such vectors or the introduction of the resulting plasmids into the *F. heparinum* hosts. The Examples also do not include detailed description for conventional methods employed to assay and identify the polypeptides produced by such host vector systems. Such methods are well known to those of ordinary skill in the art and are described in numerous publications.

Example 1

*F. heparinum* Plasmid Systems pBBRICm is a derivative of the plasmid pBBR1 with a gene coding for chloramphenicol resistance cloned in. It is a cryptic plasmid isolated from *Bordetella bronchiseptica* S87. It is further a broad-host-range plasmid known to replicate in *E. coli.* pIBXF2 has the following characteristics:

(1) a bla gene coding for β lactamase (conferring ampicillin resistance)—functional in *E. coli;*

(2) an ORI T region—allows for the mobilization of the plasmid into a new host (a Sau3 AI 307bp fragment isolated from plasmid RP4);

(3) a dhfrII gene coding for dihydrofolate reductase type II (conferring trimethoprim resistance)—cloned from plasmid R751 and placed under the control of the hepA promoter—functional in *F. heparinum;*

(4) a hepA promoter—an 830 bp fragment 5' of the hepA gene—induced by heparin;

(5) a unique restriction site (for example, a XbaI site)—site for insertion of all homologous and heterologous genes;

(6) a rep gene—involved in the replication of the plasmid; and (7) a putative ORI—functional in both *E. coli* and *F. heparinum*—A-T rich region common to ORI C.

pIBXF2 was constructed, using methods known in the art, fusing portions of pIBXF1 and pBBRICm. DNA amplification was used to generate a fragment from pIBXF1 which included the region from the ampicillin resistance marker to the XbaI site (see FIG. 2)—the ColEI ORI was not included. This fragment was inserted into pBBRICm within the gene encoding chloramphenicol resistance (not shown) disrupting it.

Once pIBXF2 was constructed, homologous genes cslA ad cslB were separately cloned into the plasmid. The homologous genes were under the control of the hepA gene promoter.

The following heterologous gene has been cloned into the vector: dhfrII.

Example 2

*F. heparinum* Integration Vector

The integration vector, pIBXF1, was created by the addition of various elements to the parent plasmid, pUC13T.

The following elements are present on the parent plasmid:

(1) bla gene coding for β-lactamase (conferring ampicillin resistance)—functional in *E. coli.*

(2) ColEI ORI—origin of replication—functional in *E. coli.*

(3) ORI T region allows for the mobilization of the plasmid into a new host (a Sau3 AI 307 bp fragment isolated from plasmid RP4).

The following elements were introduced into the pUC13T plasmid to confer integrative and selective functions in *F. heparinum.*

(1) 10 kb HindIII fragment—a 10 kb fragment randomly selected from genomic *F. heparinum* DNA which was digested with HindIII, and cloned into pUC13T.

(2) dhfrII gene coding for dihydrofolate reductase type II (conferring trimethoprim resistance)—cloned from plasmid R751 and placed under the control of the hepA promoter—functional only in *F. heparinum.*

(3) hepA promoter—an 830 bp fragment 5' of the hepA gene—induced by heparin.

Once the *F. heparinum* integration vector was constructed (see FIG. 1), homologous genes cslA, cslB, hepA, hepB, and hepc were separately cloned into the vector. The homologous genes were placed under the control of the hepA promoter.

The heterologous genes dhfrII and lacZ were also cloned into the vector.

Example 3

Introduction of Recombinant DNA into *F. heparinum*

Conjugation:

Plasmids were introduced into the *E. coli* strain S17-1. S17-1 is a mobilizing strain which provides, in trans, the genes needed for conjugative DNA transfer.

Overnight cultures of both *F. heparinum* and *E. coli* S17-1 containing the plasmid DNA were subcultured to an $OD_{600}$ of 0.1 and grown to a mid-log phase of $OD_{600}$ of 0.5. *F. heparinum* was grown in MG media supplemented with 1% heparin, 0.02% methionine/histidine, and 2 mM $MgSO_4$ at 23° C. *E. coli* was grown in Lauria-broth supplemented with 50 μg/mL ampicillin and 10 μg/mL trimethoprim at 37° C.

1.75 mL of *F. heparinum* and 100 μL of *E. coli* were combined in a 2 mL eppendorf tube and spun at 2500 g for 3 minutes. The cell pellet was resuspended in 100 μL MG and spread over a 0.45 mm membrane (Millipore, catalog number HAWG 025 00) which was placed on an agar petri dish (preheated for 30 minutes at 30° C.) containing LB/MG medium supplemented with 1% heparin, and 50 μg/mL ampicillin and incubated overnight at 30° C. As a negative control, 1.75 mL of *F. heparinum* was treated as above.

Bacteria which grew on the membrane were harvested by placing the membrane into 1 mL of MG and vortexing until bacteria could no longer be seen on the membrane. The bacteria were then placed on selective agar plates (called MGHKT) consisting of MG medium supplemented with 1% heparin, 0.02% methionine/histidine, 2 mM $MgSO_4$, 100 µg/mL gentamicin, 100 µg/mL kanamycin, and 0.6 mg/mL trimethoprim. The cells were plated at the following ratios: 1/5, 3/10, and ½ of the total harvested cell volume. The plates were then incubated at 23° C. for approximately 5 to 7 days until colonies were visible.

Electroporation:

*F. heparinum* cells were made electro-competent according to the method described by Sambrook et al., supra. The DNA and 40 µL of electro-competent *F. heparinum* (thawed on ice) were combined in a pre-chilled (on ice) 1.5 mL eppendorf tube and allowed to sit on ice for approximately 1 minute. This mixture was then placed in a pre-chilled (on ice) electroporation cuvette with a 0.2 cm electrode gap (Bio-Rad Laboratories, catalogue number 165-2086). The cuvette was placed in a Gene-Pulser electroporation apparatus (Bio-Rad Laboratories, catalogue number 165 2098). A resistance of 400 Ω with a capacitance of 25 µFD and a voltage of 2.5 kV was applied to the cells for a field strength of 12.5 kV/cm. The cells were then immediately resuspended in 1 mL Lauria-broth supplemented with 1% heparin and incubated at 30° C. for 4–6 hours. The cells were then microfuged at 2500 g for 3 minutes and plated on MGHKT selective plates. The plates were incubated at 23° C. for 5–7 days until colonies became visible.

Example 4

Expression of Proteins in *F. heparinum*

The following proteins have been expressed in *F. heparinum* using the integration vector, pIBXF1, containing the genes described below:

cslA gene with GenBank accession number U27583; coding for the chondroitinase AC protein.

cslB gene with GenBank accession number U27584; coding for the chondroitinase B protein.

epB gene with GenBank accession number U27585; coding for the heparinase II protein.

hepC gene with GenBank accession number U27586; coding for the heparinase III protein.

hepA gene with GenBank accession number L12534; coding for the heparinase I protein.

lacZ gene with GenBank accession number L08936 (plasmid pMC 1871).

The proteins which have been expressed in *F. heparinum* using the plasmid system, pIBXF2, are those of the following genes' products:

cslA gene with GenBank accession number U27583; coding for the chondroitinase AC protein.

cslB gene with GenBank accession number U27584; coding for the chondroitinase B protein.

Also, the trimethoprim resistance gene, dhfrII, from plasmid R751 was expressed in both systems.

All genes were placed under control of the hepA promoter, with the exception of lacZ, which was placed under the control of the *F. heparinum* lysA promoter. In the case of the genes coding for the chondroitinases and heparinases, their respective leader peptides were included.

The GAG lyase proteins mentioned above, with the exception of heparinase III, were glycosylated, as were the native proteins isolated from *F. heparinum*. These proteins were further characterized by SDS-PAGE analysis for molecular weight, Western analysis using polyclonal antibodies specific for non-glycosylated moieties of the various proteins, and by enzymatic assays in which the appropriate substrate was degraded by the enzyme. In all cases, the transconjugate protein products behaved in the same manner as their native counterparts with the exception that greater specific activities (IU $ml^{-1}OD_{600}^{-1}$) were seen for the transconjugate proteins.

The dhfrII gene protein product was characterized by the ability of the transconjugate colony to be resistant to high levels of trimethoprim, i.e. 0.6 mg/mL.

Example 5

Culturing of *F. heparinum*

*F. heparinum*, ATCC 13125, produces heparinases I, II, and III, and chondroitinases AC and B. It is also referred to as *Cytophaga heparina* (Ref. Christensen, 1980, Int. J. Syst. Bacteriol. 30:473–475); *Sphingobacterium heparinum* (Ref. Takeuchi and Yokota, 1992, J. Gen. Appl. Microbiol. 38:465–482); or *Pedobacter heparinus* (Ref Steyn et al., 1998, Int. J. Syst. Bacteriol., 48:165–177).

*F. heparinum* cells can be cultured in an ordinary medium containing a carbon source, nitrogen source, and inorganic salts. As a carbon source, any of those which can be assimilated can be used, for example, D-glucose, maltose, D-xylose, sucrose, heparin, citrate, succinate, glutamate, tryptone, or peptone are typical examples. As a nitrogen source, various conventional materials can be used, for example, yeast extract, peptone, meat extract, amino acids or organic nitrogen such as ammonia sulfate or ammonium chloride. In addition, various salts may be added, for example, inorganic salts such as magnesium sulfate, magnesium chloride, potassium chloride, calcium chloride, potassium phosphate, and sodium phosphate. Vitamins and other growth factors are not essential but may be added, for example, folic acid, calcium pantothenate, biotin, riboflavin, and thiamine. It is further possible to add a gelling agent when desired, such as agar, gelatin, and gellan gum. The medium is adjusted to a final pH of 5.5 to 8.5, preferably pH 7.0, by addition of an acid or base as appropriate.

As a specific example of a suitable defined medium, a liquid medium containing (per liter) 6 g $K_2HPO_4$, 3 g $KH_2PO_4$-$H_2O$, 1 g NaCl, 2 g $NH_4Cl$, 2 mM $MgSO_4$-$7H_2O$, 0.4 g L-histidine, 0.4 g L-methionine, 16 g glucose, 2 g heparin, $10^{-4}$ mM each of $NaMoO_4$-$2H_2O$, $CoCl_2$-$6H_2O$, $MnSO_4$-$7H_2O$, $CuSO_4$-$5H_2O$, $FeSO_4$-$7H_2O$ and $CaCl_2$. The organism can be stored for up to two weeks on agar plates containing 1% Difco agar in defined medium, containing 4 g heparin/L as the sole carbon source, or the organism can be stored indefinitely in 10% glycerol at −80° C.

Example 6

Purification of Proteins from *F. heparinum*

Methods which have been used to extract proteins from the periplasmic space of Gram negative bacteria include osmotic shock treatment as the initial step. Typically these procedures include an initial disruption in osmotically stabilizing medium followed by selective release in non-stabilizing medium. The composition of these media (pH, protective agent) and the disruption methods used (chloroform, lysozyme, EDTA, sonication) vary among specific procedures reported.

*F. heparinum* cells can be concentrated by ultrafiltration, and subjected to osmotic shock treatment to release proteins from the periplasmic space. Disruption of the cell envelope can be induced by exposing the cells to an osmotically stabilized medium (containing 20% sucrose) with or without EDTA, followed by an initial release of periplasmic material into a non-stabilized medium (10 mM phosphate, at a pH between 6.0 and 8.6) with a subsequent release into a second non-stabilized medium (10 mM phosphate, 150 mM sodium chloride, at a pH between 6.0 and 8.6). This three step procedure can provide an initial fraction of the proteins in the periplasmic space. As will be apparent to one skilled in the art, the purification method used will depend on the identity of the foreign protein.

We claim:

1. A *Flavobacterium heparinum* host cell transformed with a recombinant DNA expression vector selected from the group consisting of pIBFX1 and pIBFX2.

2. The host cell of claim 1, wherein said recombinant DNA is integrated into the *Flavobacterium heparinum* chromosome.

3. The host cell of claim 2, wherein said recombinant DNA is integrated through homologous recombination.

4. The host cell of claim 2, wherein a gene in said integrated DNA is expressed at high levels.

5. The host cell of claim 1, wherein said recombinant DNA is introduced into said cell by conjugation.

6. A *Flavobacteriun heparinum* host cell transformed with a recombinant DNA expression vector effective to cause expression of at least one protein encoded by a homologous or heterologous coding sequence selected from the group consisting of heparinase I, heparinase II, and heparinase III, wherein said recombinant DNA expression vector is selected from the group consisting of pIBFX1 and pIBFX2.

7. A *Flavobacterium heparinum* host cell transformed with a recombinant DNA expression vector effective to cause expression of at least one selectable marker protein encoded by a homologous or heterologous coding sequence, wherein said recombinant DNA expression vector is selected from the group consisting of pIBFX1 and pIBFX2.

8. A *Flavobacterium heparinum* host cell transformed with a recombinant DNA expression vector effective to cause expression of at least one protein encoded by a homologous or heterologous coding sequence selected from the group consisting of heparinase I, heparinase II, heparinase III, and selectable markers, regulated by a regulatory region effective in *Flavobacterium heparinum*, wherein said recombinant DNA expression vector is selected from the group consisting of pIBFX1 and pIBFX2.

9. An expression system for expressing a desired polypeptide or protein comprising a *F. heparinum* host organism; nucleotide sequences encoding at least one desired polypeptide or protein selected from the group consisting of heparinase I, heparinase II, heparinase III, and selectable markers; and an expression vector for expressing the nucleotide sequences capable of expressing the desired polypeptide or protein, wherein the expression vector is selected from the group consisting of pLBFX1 and pIBFX2.

* * * * *

UNITED STATES PATENT AND TRADEMARK OFFICE
CERTIFICATE OF CORRECTION

PATENT NO. : 6,841,375 B2
DATED : January 11, 2005
INVENTOR(S) : Hongsheng Su et al.

It is certified that error appears in the above-identified patent and that said Letters Patent is hereby corrected as shown below:

<u>Title page,</u>
Item [73], Assignee, please change "Pharmaceuticals" to -- Pharmaceutical --.

Signed and Sealed this

Tenth Day of May, 2005

JON W. DUDAS
*Director of the United States Patent and Trademark Office*